(12) United States Patent
Buckley et al.

(10) Patent No.: US 10,695,203 B2
(45) Date of Patent: Jun. 30, 2020

(54) ENDOPROSTHESIS HAVING ALIGNED LEGS FOR EASE OF CANNULATION

(71) Applicant: W. L. Gore & Associates, Inc., Newark, DE (US)

(72) Inventors: Kyle R. Buckley, Flagstaff, AZ (US); Benjamin I. Espen, Flagstaff, AZ (US); Douglas C. Helsel, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/266,308

(22) Filed: Feb. 4, 2019

(65) Prior Publication Data

US 2019/0167458 A1    Jun. 6, 2019

Related U.S. Application Data

(60) Continuation of application No. 15/632,741, filed on Jun. 26, 2017, now Pat. No. 10,195,063, which is a
(Continued)

(51) Int. Cl.
*A61F 2/95* (2013.01)
*A61F 2/954* (2013.01)
(Continued)

(52) U.S. Cl.
CPC ............. *A61F 2/954* (2013.01); *A61F 2/07* (2013.01); *A61F 2/97* (2013.01);
(Continued)

(58) Field of Classification Search
CPC .... A61F 2/07; A61F 2/95; A61F 2/954; A61F 2/958; A61F 2002/9511
See application file for complete search history.

(56) References Cited

U.S. PATENT DOCUMENTS 6,102,940 A    8/2000   Robichon
6,165,210 A *  12/2000  Lau ........................ A61F 2/88
                                                     623/1.12
(Continued)

FOREIGN PATENT DOCUMENTS

EP    1474074 B1    4/2004
EP    1441668 B1    1/2008
(Continued)

OTHER PUBLICATIONS

International Search Report & Written Opinion from PCT/US2018/034399, dated Nov. 9, 2018, 13 pages.
(Continued)

*Primary Examiner* — Christopher D. Prone
*Assistant Examiner* — Tiffany P Shipmon (57) ABSTRACT

The present disclosure is directed to a branched endoprosthesis comprising a graft component and at least one support component. In various embodiments, the branched endoprosthesis comprises a body portion and a plurality of leg portions, wherein the legs are in an aligned configuration for ease of cannulation. In various embodiments, at least one leg is in an open configuration for ease of cannulation. Cannulation methods are also described.

20 Claims, 6 Drawing Sheets

Related U.S. Application Data division of application No. 13/740,457, filed on Jan. 14, 2013, now Pat. No. 9,687,371.

(60) Provisional application No. 61/598,773, filed on Feb. 14, 2012.

(51) Int. Cl.
*A61F 2/07* (2013.01)
*A61F 2/97* (2013.01)
*A61F 2/06* (2013.01)

(52) U.S. Cl.
CPC ... *A61F 2002/065* (2013.01); *A61F 2002/072* (2013.01); *A61F 2002/9511* (2013.01); *A61F 2210/009* (2013.01); *A61F 2210/0014* (2013.01); *A61F 2220/005* (2013.01); *A61F 2220/0058* (2013.01)

(56) References Cited

U.S. PATENT DOCUMENTS

| | | | |
|---|---|---|---|
| 6,203,550 | B1 | 3/2001 | Olson |
| 6,264,662 | B1 | 7/2001 | Lauterjung |
| 6,368,345 | B1 | 4/2002 | Dehdashtian |
| 6,733,521 | B2 | 5/2004 | Chobotov et al. |
| 6,911,039 | B2 | 6/2005 | Shiu |
| 6,974,471 | B2 | 12/2005 | Van Schie |
| 7,081,132 | B2 | 7/2006 | Cook |
| 7,147,661 | B2 | 12/2006 | Chobotov |
| 7,655,034 | B2 | 2/2010 | Mitchell et al. |
| 7,837,724 | B2 | 11/2010 | Keeble |
| 7,938,851 | B2 | 5/2011 | Olson |
| 7,976,575 | B2 | 7/2011 | Hartley |
| 8,167,927 | B2 | 5/2012 | Chobotov |
| 8,241,346 | B2 | 8/2012 | Chobotov |
| 8,257,431 | B2 | 9/2012 | Henderson |
| 8,262,671 | B2 | 9/2012 | Osypka |
| 8,328,861 | B2 | 12/2012 | Martin |
| 8,361,135 | B2 | 1/2013 | Dittman |
| 8,480,725 | B2 | 7/2013 | Rasmussen |
| 8,968,384 | B2 | 3/2015 | Pearson |
| 9,060,895 | B2 | 6/2015 | Hartley |
| 9,132,025 | B2 | 9/2015 | Aristizabal |
| 9,254,204 | B2 | 2/2016 | Roeder |
| 9,308,349 | B2 | 4/2016 | Rezac |
| 9,364,359 | B2 | 6/2016 | Crawford |
| 9,498,361 | B2 | 11/2016 | Roeder |
| 9,585,743 | B2 | 3/2017 | Cartledge |
| 9,585,774 | B2 | 3/2017 | Aristizabal |
| 9,681,968 | B2 | 6/2017 | Goetz |
| 9,700,701 | B2 | 7/2017 | Benjamin |
| 9,782,284 | B2 | 10/2017 | Hartley |
| 9,937,070 | B2 | 4/2018 | Skelton |
| 2002/0029077 | A1 | 3/2002 | Leopold et al. |
| 2003/0120333 | A1 | 6/2003 | Ouriel |
| 2004/0167618 | A1 | 8/2004 | Shaolian |
| 2004/0243221 | A1 | 12/2004 | Fawzi |
| 2005/0149081 | A1 | 7/2005 | Ricot |
| 2006/0002851 | A1 | 1/2006 | Langstrom et al. |
| 2006/0025850 | A1 | 2/2006 | Feller |
| 2006/0025851 | A1 | 2/2006 | Khan |
| 2007/0050015 | A1 | 3/2007 | O'Brien |
| 2009/0099649 | A1 | 4/2009 | Chobotov |
| 2009/0125095 | A1 | 5/2009 | Bui |
| 2009/0299462 | A1* | 12/2009 | Fawzi .................. A61F 2/07 623/1.13 |
| 2013/0211501 | A1 | 8/2013 | Buckley |
| 2013/0338760 | A1 | 12/2013 | Aristizabal |
| 2017/0172724 | A1 | 6/2017 | Cartledge |
| 2017/0281382 | A1 | 10/2017 | Lostetter |

FOREIGN PATENT DOCUMENTS

| | | | |
|---|---|---|---|
| EP | 2111828 | A2 | 10/2009 |
| EP | 1915113 | B1 | 3/2010 |
| EP | 1358903 | B1 | 2/2011 |
| EP | 2749251 | B1 | 7/2016 |
| EP | 2956198 | B1 | 11/2017 |
| JP | 2006-34970 | | 2/2006 |
| JP | 2010-540190 | | 12/2010 |
| WO | WO-2003045284 | A2 | 6/2003 |
| WO | WO-2004047885 | A2 | 6/2004 |
| WO | WO-2007025101 | A2 | 3/2007 |
| WO | WO-2009046372 | | 4/2009 |
| WO | WO-2009058369 | | 5/2009 |
| WO | WO-2014096811 | A2 | 6/2014 |

OTHER PUBLICATIONS

International Search Report for PCT/US2013/021528 dated Jun. 19, 2013, 11 pages.

* cited by examiner

ENDOPROSTHESIS HAVING ALIGNED LEGS FOR EASE OF CANNULATION

CROSS-REFERENCE TO RELATED APPLICATION

This application is a continuation of U.S. patent application Ser. No. 15/632,741, filed Jun. 26, 2017, now U.S. Pat. No. 10,195,063, issued Feb. 5, 2019, which is a divisional of U.S. patent application Ser. No. 13/740,457, filed Jan. 14, 2013, now U.S. Pat. No. 9,687,371, granted Jun. 27, 2017, which claims priority to and the benefit of U.S. Provisional Patent Application Ser. No. 61/598,773, filed Feb. 14, 2012, all of which are incorporated by reference herein in their entireties.

FIELD

The present disclosure relates to improved branched endoprostheses for treating disease of the vasculature.

DISCUSSION OF THE RELATED ART

Branched endoprostheses are commonly used for treating disease of the vasculature. By way of example, bifurcated stent grafts may be used in the treatment of abdominal aortic aneurisms, which generally affect the abdominal aorta and may extend down into the iliac arteries.

A bifurcated stent graft used in the treatment of abdominal aortic aneurisms is generally inserted through an iliac artery up into the abdominal aorta, where it is deployed and anchored. The graft's ipsilateral leg extends down into the iliac artery through which the graft was inserted. On the other hand, the graft's contralateral leg does not extend below the abdominal aorta.

To extend the graft's contralateral leg down into the other iliac artery, a second stent graft is inserted through that other iliac artery over a guidewire and attached to the original graft's contralateral leg. Although endoscopic imaging, radiopaque markers, etc. may be employed, this cannulation process is often difficult given not only the tortuous vasculature, but also structural biases within the original stent graft angling the legs apart in a Y configuration so as to face them toward their respective iliac arteries.

Generally speaking, cannulation of contralateral legs of branched endoprostheses presents difficulties for medical practitioners who heretofore have had to rely heavily on trial and error. There is thus a need in the art for bifurcated endoprostheses that are better adapted for ease of cannulation.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

In addition, the present disclosure will be described primarily with reference to treating disease of the abdominal aorta, however, the disclosure and principles may be applied to other disease of the vasculature, including, for example, any disease where a larger vessel and one or more branch vessels are to be treated. Likewise, although the disclosure will be described primarily with reference to bifurcated endoprostheses, it should be understood that the disclosure and principles may be applied to endoprostheses having any number of branches, for example, 2, 3, 4 or more.

The present disclosure is directed toward a branched endoprosthesis. An endoprosthesis may comprise a graft component and at least one support component, such as in a stent graft.

A graft component is generally any abluminal (i.e., outer, vessel surface) or luminal (i.e., inner, blood flow surface) covering configured to partially or substantially cover one or more support components.

In various embodiments, a graft component comprises ePTFE. However, other useful materials for the graft component may comprise one or more of nylons, polycarbonates, polyethylenes, polypropylenes, polytetrafluoroethylenes, polyvinyl chlorides, polyurethanes, polysiloxanes, and other biocompatible materials.

A graft component is fixedly secured or otherwise coupled at a single or a plurality of locations to the abluminal or luminal surface of the support component, for example, using one or more of taping, heat shrinking, adhesion and other processes known in the art. In some embodiments, a plurality of graft components are used and may be coupled to both the abluminal and luminal surfaces of the support component(s). In other embodiments, a plurality of graft components "sandwich" the support component(s), the graft components being attached to each other.

In various embodiments, a support component has dimensions appropriate for the given treatment and may provide structural support for the graft component of the endoluminal device and/or the vasculature to be treated. A support component may be a stent comprised either of a wire having a helical configuration or be comprised of one or a plurality of rings. Among other configurations, the wire or a ring itself may be linear or have a sinusoidal or zig-zag pattern. Still another support component may be cut from a tube and have any pattern suitable for the treatment.

The support component can be comprised of a shape-memory material, such as nitinol. In other embodiments, however, the support component may be comprised of other materials, self-expandable or otherwise expandable (e.g., with a conventional balloon catheter or spring mechanism), such as various metals (e.g., stainless steel), alloys and polymers.

In various embodiments, the branched endoprosthesis comprises a body portion and at least two leg portions, which may be defined by the graft and/or support components. The cross-section of the body portion may be circular, ovoidal, or have polygonal features with or without curved features. The cross-sectional shape of the body portion may be either substantially constant or variable along its axial length. In like manner, the cross-sectional surface area of the body portion may be either substantially constant or variable along its axial length. In an embodiment of a bifurcated endoprosthesis, the body portion's cross-section is substantially circular at its distal end but tapers to have an ovoidal rectangular cross-section with a smaller cross-sectional surface area in its bifurcation region.

As noted previously, a branched endoprosthesis comprises two or more leg portions branched off of and in luminal communication with the body portion.

In various embodiments, the axial length(s) of the contralateral leg(s) (i.e., the leg(s) for cannulation) is/are substantially shorter that the axial length of the ipsilateral leg.

In various embodiments, a branched endoprosthesis possesses one or more structural biases angling the leg portions apart, for instance in a Y configuration, so as to face or direct them toward their respective vessels to be treated. The structural bias may arise from either or both of a graft component and a support component.

In various embodiments, at least two leg portions are in an aligned configuration for ease of cannulation. The alignment may be permanent or in some embodiments, temporary until after guidewire insertion or cannulation. In various embodiments, aligning a plurality of leg portions requires overcoming the aforementioned structural bias. As used herein, "align" or "aligned" means aligned axially, drawn together, parallel, and/or the state of the plane of the contralateral leg's opening being perpendicular to the axis of the ipsilateral leg. For the avoidance of doubt, "align" may, but does not necessarily implicate alignment along or with respect to any anatomical or endoprosthesis axis.

Figure 1A:
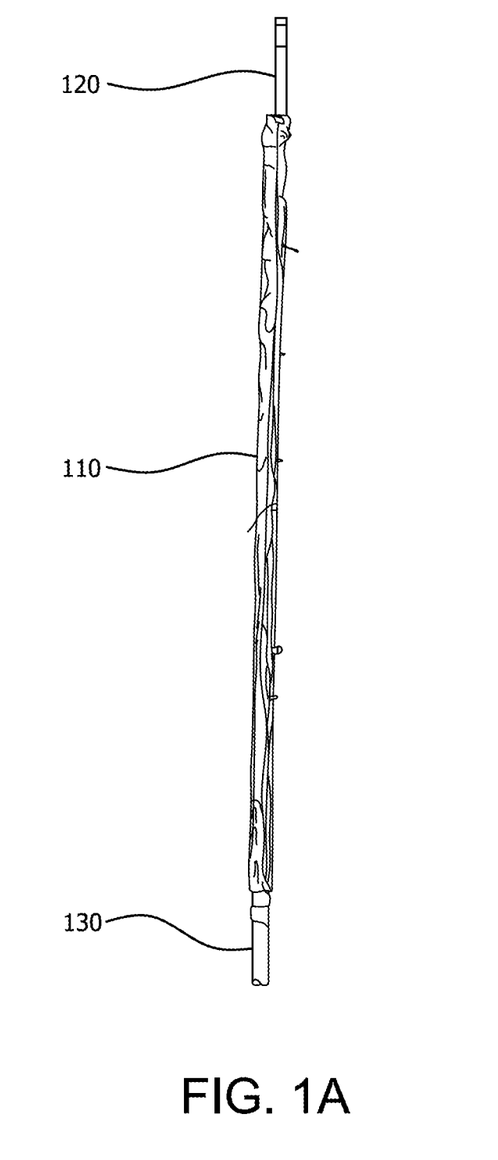
FIGS. 1A-1E illustrate the progressive deployment of a branched endoprosthesis having two legs in an aligned configuration in accordance with one embodiment of the present disclosure.

In an embodiment, alignment is accomplished by commonly sheathing the legs and only removing the sheath after guidewire insertion or cannulation. For example, and with reference to the accompanying drawings, FIG. 1A illustrates an outer sheath 110 enclosing a bifurcated stent graft (not shown) to be delivered via a guidewire 120 and a tubular element 130.

A "sheath" may be comprised of one or more of nylons, polycarbonates, polyethylenes, polypropylenes, polytetrafluoroethylenes, polyvinyl chlorides, polyurethanes, polysiloxanes, stainless steels, or other biocompatible materials. A sheath can be a sleeve or an introducer sheath. In yet other embodiments, a sheath is a tubular element, as that term has been defined herein.

The term "tubular element" includes any longitudinally extending structure with or without a lumen therethrough, for example a catheter. Thus, tubular elements include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Tubular elements can be of any material and can have any cross-sectional shape including but not limited to profiles that are circular, oval, triangular, square, polygon shaped or randomly shaped.

Figure 1B:
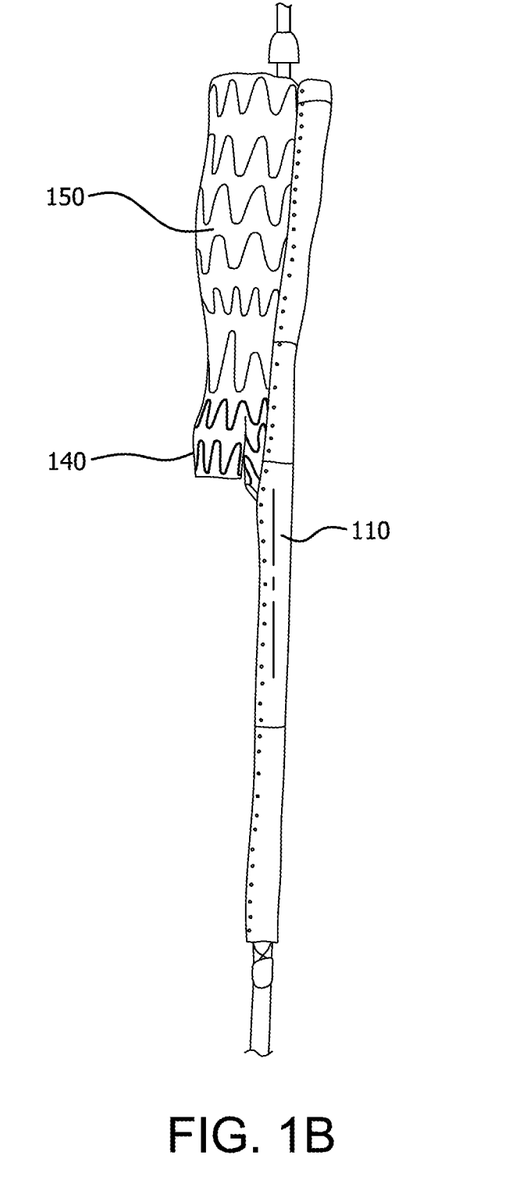

Turning now to FIG. 1B, outer sheath 110 may be partially removed from the distal half of bifurcated stent graft 140, revealing a closed inner sheath 150 which aligns the contralateral and ipsilateral legs of bifurcated stent graft 140.

Figure 1C:
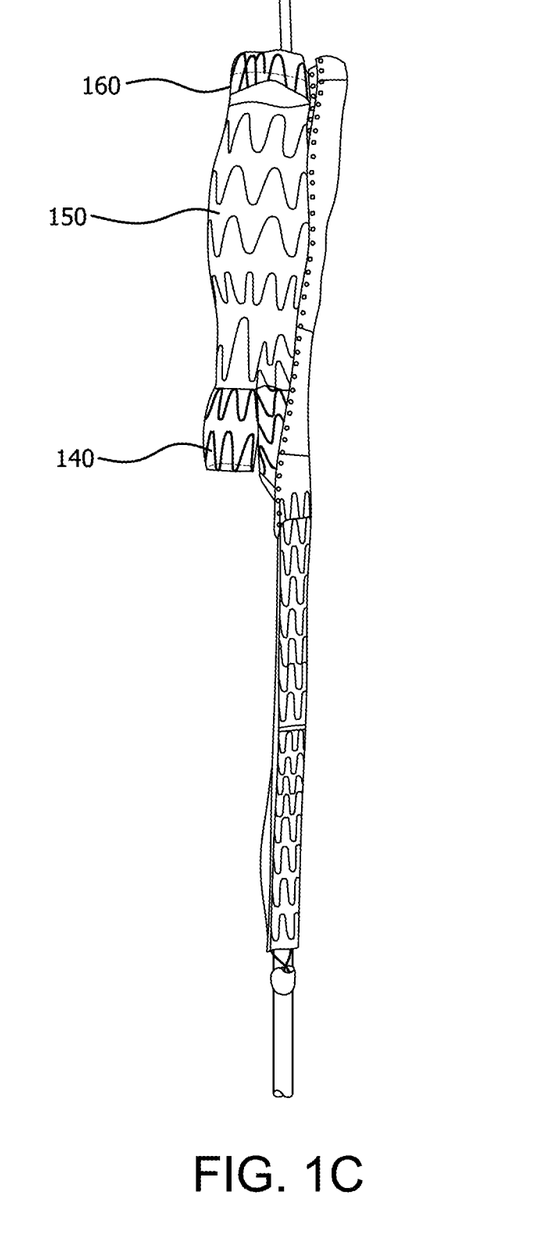

With reference to FIG. 1C, anchors 160 at the distal end of bifurcated stent graft 140 may be retracted for adjusting placement of bifurcated stent graft 140. Note that in this embodiment, inner sheath 150 still maintains the contralateral and ipsilateral legs of bifurcated stent graft 140 in an aligned configuration.

Figure 1D:
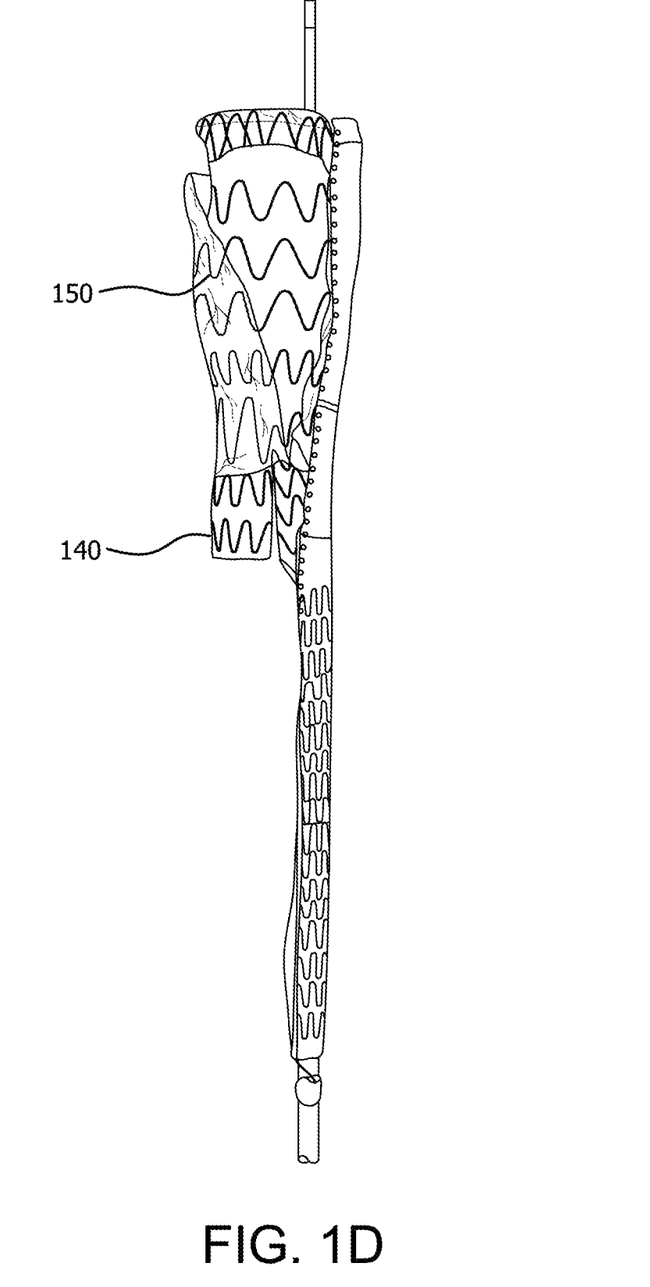
Figure 1E:
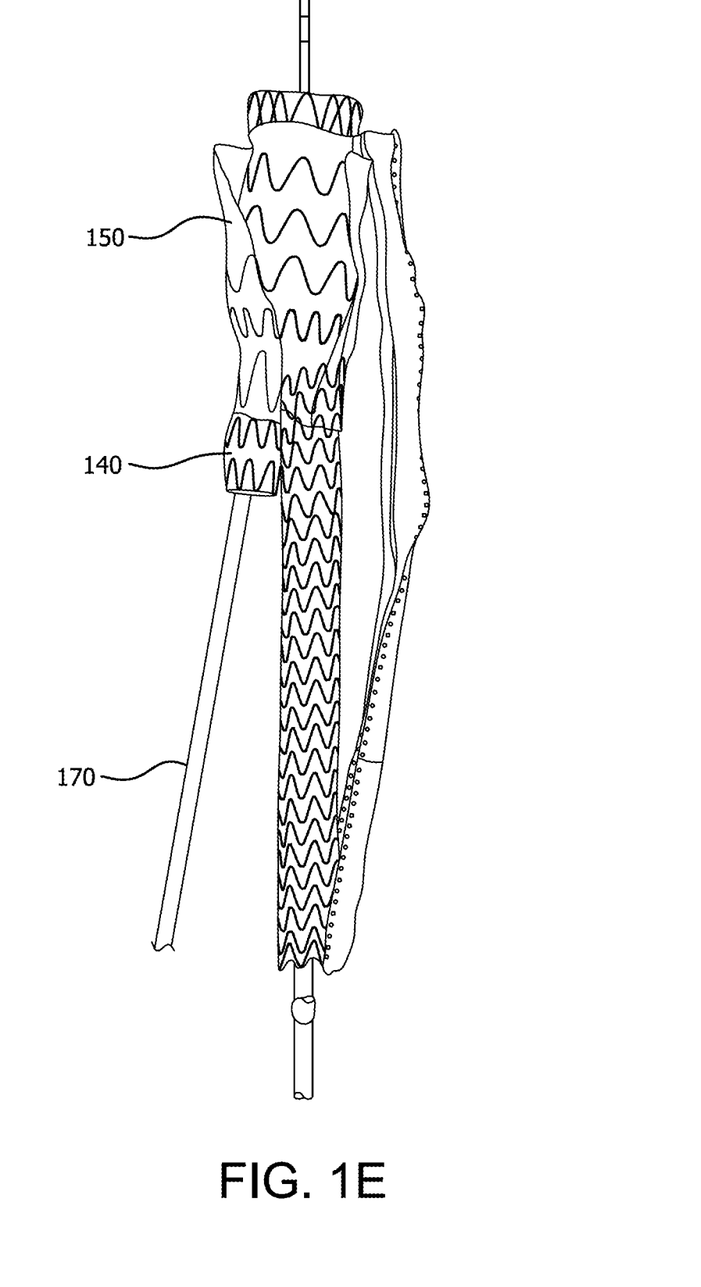

As shown in FIG. 1D, inner sheath 150 may be partially removed from the distal portion of bifurcated stent graft 140, but not removed at its proximal end, thus maintaining the contralateral and ipsilateral legs of bifurcated stent graft 140 in an aligned configuration until, as shown in FIG. 1E, a guidewire 170 has been inserted into the contralateral leg of bifurcated stent graft 140 or cannulation of the contralateral leg has occurred.

Notwithstanding the foregoing non-limiting example, various physical and chemical coupling methods and apparatuses may be used in the alignment, including but not limited to various removable tethers, restraints, adhesives, hooks, magnets, nanostructure binding agents, etc.

Figure 2A:
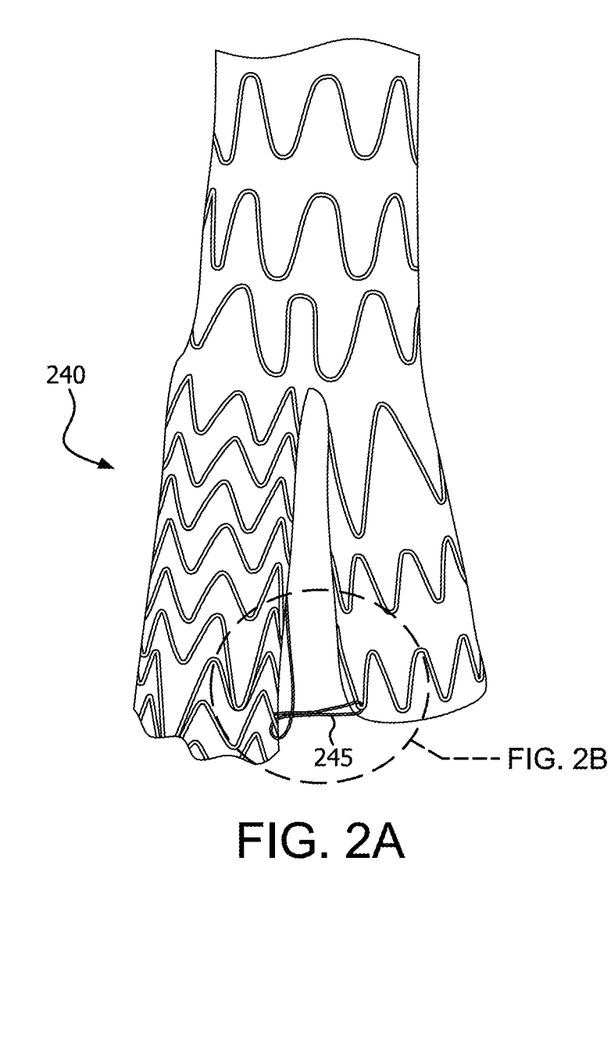
FIGS. 2A and 2B illustrate a tether configured to maintain contralateral and ipsilateral legs of a bifurcated stent graft in an aligned configuration in accordance with one embodiment of the present disclosure.
Figure 2B:
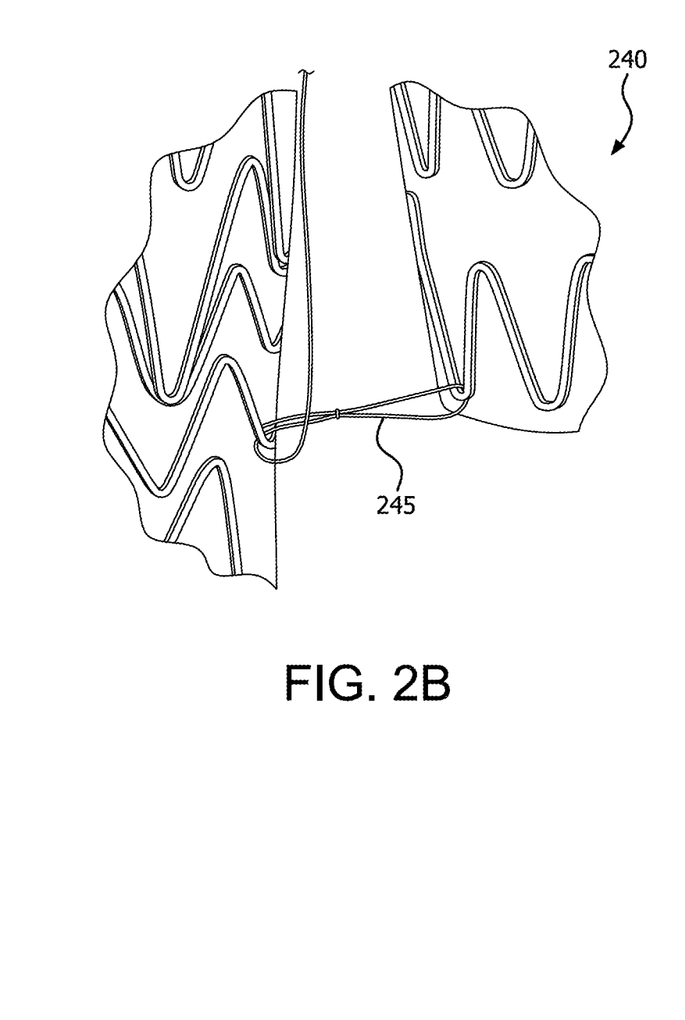

FIGS. 2A and 2B illustrate a tether 245 configured to maintain contralateral and ipsilateral legs of a bifurcated stent graft 240 in an aligned configuration in accordance with one embodiment of the present disclosure. In various embodiments, tether 245 releasably couples and retains contralateral and ipsilateral legs of bifurcated stent graft 240 including, in various embodiments, during movement of bifurcated stent graft 240 between delivery and deployed configurations.

In various embodiments, an outer sheath extends around and maintains bifurcated stent graft 240 in a delivery configuration. In such embodiments, the outer sheath can have opposite sides releasably held together to maintain bifurcated stent graft 240 in the delivery configuration. In such embodiments, the outer sheath can have a plurality of holes through which an elongated member extends to releasably hold the opposite sides of the outer sheath together. In such embodiments, tether 245 can be an extension of the elongated member.

An end tail of tether 245 can be tucked under undeployed portions of a surrounding sleeve and/or routed under, or otherwise secured to, one or more apices of a support component. Tether 245 can be routed in various configurations, for example between an apice of a support component and the wall of a graft component. In general, an end tail of tether 245 is routed so as to be retained, while not presenting high pullout forces.

Tether 245 can comprise a thread, fiber, or filament, for example one that is polymeric in nature. In other embodiments, tether 245 comprises a wire, having a high columnar strength. In yet other embodiments, tether 245 is a tubular element, as that term has been defined herein.

In various embodiments, tether 245 is adjustable separate from being pulled out. In various embodiments, tether 245 is pulled out separate from deployment of bifurcated stent graft 240.

In various embodiments, tethering eliminates the need for an inner sheath, thus reducing the crossing profile, for example to less than 18 Fr, less than 16 Fr, or less than 14 Fr.

Adhesives may comprise those that are soluble for releasing the legs from their aligned configuration after guidewire insertion or cannulation. A single hook or a plurality of hooks or hook and loop fasteners (e.g., a Velcro® type configuration) may be used. A magnet may be inserted via catheter into the one leg to draw another leg into alignment with it. Nanostructure binding agents useful in the alignment may comprise DNA, RNA, etc.

Additional features and elements may be used in connection with the present disclosure. In one embodiment for example, at least one leg is maintained in an open configuration for ease of cannulation. This may be accomplished, for example, by incorporating an independent wire or ring, such as a support component as described herein, at the distal end of the leg. In an embodiment, a plurality of serially aligned support components are adapted to hold the contralateral leg open for cannulation. In yet another embodiment, one or more radiopaque and/or echogenic markers are incorporated into the branched endoprosthesis, for example, along, or at the distal end of, the contralateral leg.

A cannulation method comprises delivering a branched stent graft enclosed by an outer sheath into a branch artery and to the lumen of a trunk artery via a guidewire and a tubular element, for example at a distal end of a catheter.

In various embodiments, the outer sheath is partially removed from the body portion of the branched stent graft extending into the trunk artery, thus partially deploying the graft and exposing an inner sheath which aligns one or more contralateral legs with the ipsilateral leg of the branched stent graft.

Next, placement of the branched stent graft may be adjusted, for example, by retracting anchors at the distal end of the body portion of the branched stent graft, rotating and/or advancing or reversing the guidewire and/or the tubular element, and thereafter fully deploying the anchors into the sides of the trunk artery.

Once the branched stent graft is determined to be properly positioned, a second guidewire may be inserted into a contralateral leg of the branched stent graft via a second branch artery in communication with the trunk artery. Cannulation of the contralateral leg may thereafter occur.

Once the second guidewire has been inserted into the contralateral leg, the inner sheath may be fully removed, thus no longer necessarily maintaining the contralateral and ipsilateral legs of the branched stent graft in an aligned configuration.

Yet another method comprises providing a branched stent graft comprising a body portion, an ipsilateral leg portion, and a contralateral leg portion. In this particular embodiment, the leg portions may be biased to be angled apart in a Y configuration. Next, the bias is temporarily overcome by aligning the leg portions using one or more of the mechanisms described herein.

In accordance with this method, the branched stent graft is delivered to a trunk vessel via an ipsilateral branch vessel. The body portion and the ipsilateral leg portion of the branched stent graft are deployed in the trunk vessel and the ipsilateral branch vessel respectively. Using the alignment of the leg portions, a distal opening of the contralateral leg portion is located to facilitate its cannulation. Finally, the leg portions are allowed to return to the initial Y configuration.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device comprising:
a stent graft including a graft component and a support component comprising a first support component and a second support component, the stent graft having a body portion, a first leg supported by the first support component, and a second leg supported by the second support component, wherein the first leg and the second leg are structurally biased to angle apart from one another; and
a restraint aligning the first and second legs to couple together and maintain alignment of the first and second legs by temporarily overcoming the bias to assist in cannulation of the second leg during deployment of the stent graft by coupling the first support component with the second support component, wherein the restraint is configured to be removed after deployment such that first and second legs are free to angle apart from one another.

2. The medical device of claim 1, wherein the restraint comprises a tether having an end that is tucked under undeployed portions of a sleeve surrounding the stent graft.

3. The medical device of claim 1, wherein the removable restraint comprises a tether having an end that is routed between the support component and the graft component.

4. The medical device of claim 1, wherein the support component provides for the first leg and the second leg being structurally biased to angle apart in a Y configuration.

5. The medical device of claim 1, wherein the first leg is substantially axially longer than the second leg.

6. The medical device of claim 1, further comprising a sheath that is disposed about both the first leg and the second leg.

7. The medical device of claim 1, further comprising a plurality of serially aligned support components adapted to hold the second leg open for cannulation.

8. The medical device of claim 1, further comprising a radiopaque marker at the distal end of the second leg.

9. The medical device of claim 1, wherein the first and second legs extend from a first end of the body.

10. The medical device of claim 1, wherein the restraint is configured to temporarily overcome the bias by creating an alignment of the first and second legs during deployment of the stent graft such that a plane of the opening of the second leg is secured perpendicular to an axis of the first leg during deployment.

11. A medical device comprising:
a stent graft having a graft component and a support component, the stent graft having a body portion, a first leg and a second leg, the stent graft having a collapsed configuration for endoluminal delivery and an expanded configuration larger than the collapsed configuration;

a removable restraint having a first portion and a second portion extending from the first portion; and an outer sheath for releasably retaining the stent graft toward the collapsed configuration, the outer sheath having opposite sides releasably held together by the first portion of the removable restraint; wherein the second portion of the removable restraint extends between the first and second legs to couple together and maintain alignment of the first and second legs as the first portion is actuated to release the opposite sides of the outer sheath.

12. The stent graft of claim 11, wherein the first and second legs extend from a first end of the body.

13. The stent graft of claim 11, wherein the first leg is substantially axially longer than the second leg.

14. The medical device of claim 11, wherein an end of the removable restraint is tucked under undeployed portions of a sleeve surrounding the stent graft.

15. The medical device of claim 11, wherein an end of the removable restraint is tucked between the support component and the graft component.

16. The medical device of claim 11, wherein the first leg and the second leg are structurally biased to angle apart from one another in a Y configuration.

17. The medical device of claim 16, wherein the support component provides for the first leg and the second leg being structurally biased to angle apart in the Y configuration.

18. The medical device of claim 16, wherein the restraint is configured to temporarily overcome the bias by creating an alignment of the first and second legs during deployment of the stent graft such that a plane of the opening of the second leg is secured perpendicular to an axis of the first leg during deployment.

19. The medical device of claim 11, further comprising a plurality of serially aligned support components adapted to hold the second leg open for cannulation.

20. The medical device of claim 11, further comprising a radiopaque marker at the distal end of the second leg.

* * * * *